United States Patent [19]

Bele et al.

[11] Patent Number: 5,027,659
[45] Date of Patent: Jul. 2, 1991

[54] ULTRASONIC IMAGING DEVICE IN WHICH ELECTROACOUSTIC TRANSDUCERS ARE DISPOSED ON A CONVEX PROBE

[75] Inventors: Robert Bele, Chessy; Patrick Bertrand, Bourg la Reine; Jean-Pierre Ramond, Meaux, all of France

[73] Assignee: General Electric CBR SA, Les Moulinequx, France

[21] Appl. No.: 320,248

[22] Filed: Mar. 7, 1989

[30] Foreign Application Priority Data

Mar. 11, 1988 [FR] France ............................. 88 03185

[51] Int. Cl.$^5$ .......................................... G01N 29/04
[52] U.S. Cl. .................................. 73/626; 128/661.01
[58] Field of Search ..................... 73/626; 128/661.01; 367/105, 123

[56] References Cited

U.S. PATENT DOCUMENTS

| | | | |
|---|---|---|---|
| 3,938,502 | 2/1976 | Bom | 73/626 |
| 4,203,162 | 5/1980 | Clearwaters et al. | 367/105 |
| 4,253,168 | 2/1981 | Petrosky et al. | 367/123 |
| 4,462,092 | 7/1984 | Kawabuchi et al. | 73/626 |
| 4,576,045 | 3/1986 | Miller-Jones | 73/626 |
| 4,759,372 | 7/1988 | Umemura et al. | 73/626 |

FOREIGN PATENT DOCUMENTS

| | | |
|---|---|---|
| 0072287 | 2/1983 | European Pat. Off. |
| 0177407 | 4/1986 | European Pat. Off. |
| 2645738 | 4/1977 | Fed. Rep. of Germany |
| 3339838 | 5/1985 | Fed. Rep. of Germany |
| 3512519 | 10/1986 | Fed. Rep. of Germany |

Primary Examiner—John Chapman
Attorney, Agent, or Firm—Cushman, Darby & Cushman

[57] ABSTRACT

A curved acoustic probe provided with a plurality of electroacoustic transducers delivers a beam of acoustic energy which is directed by electronic scanning. Electronic scanning is carried out by utilizing only those electroacoustic transducers which are capable of insonating the target. It is thus possible to employ a large number of electroacoustic transducers in respect of each azimuth and therefore to obtain high definition. The invention applies to imaging techniques involving the use of acoustic waves such as ultrasonic waves and is primarily concerned with the field of ultrasonic medical imaging. Chief among potential applications are nondestructive testing, production of images within liquids such as, for example, underwater or ocean-bottom images.

4 Claims, 5 Drawing Sheets

ULTRASONIC IMAGING DEVICE IN WHICH ELECTROACOUSTIC TRANSDUCERS ARE DISPOSED ON A CONVEX PROBE

BACKGROUND OF THE INVENTION

1. Field of the Invention

This invention primarily relates to a probe, to an imaging device in which said probe is employed and to a method for the practical application of said device.

2. Description of the Prior Art

Various types of ultrasonic scanning probes are already known. A first known type consists of sector scanning probes or in other words probes provided either with an oscillating moving system or with a plurality of electroacoustic transducers mounted on a wheel and switched as they pass in front of an emission window. The properties of these probes lie in their high rate of acquisition and simplicity of design involving relatively simple and inexpensive signal-processing means. The coupling surface for acoustic waves is relatively small, thus making it possible to place the probe between two of the patient's ribs for cardiac observations. On the other hand, these probes have a service life of limited duration.

A second known type consists of a plurality of electroacoustic transducers. Those in common use include the linear-scan device in which provision is made for a linear strip consisting, for example, of 64 elementary electroacoustic transducers. Scanning is performed by displacing the group of active transducers at each shot or emission of ultrasound waves. This type of linear strip provides low resolution by reason of the small number of transducers employed simultaneously.

In the case of linear strips, when the beam is focused by electronic scanning and by making use of time-delays in order to compensate for path differences, the scanning angle is limited. Moreover, this solution is difficult to apply in practice as well as costly since it is necessary to have elements which induce substantial time-delays while maintaining coherence of the signal.

A tentative solution to these problems has been provided by convex strips, that is to say strips in which the transducer has been disposed on a curve and the radiating surface of which is convex. A strip of this type is described in particular in European patent No. 69,677. However, the resolution of a strip of this type is still not sufficient.

All the transducers of a strip of this type cannot insonate in all directions.

SUMMARY OF THE INVENTION

A significant feature of the present invention lies in the fact that all the transducers which are capable of insonating in one direction can be employed for the purpose of forming an image corresponding to this region. Focusing is obtained by electronic scanning involving the use of delay elements. The time-delays to be achieved are shorter than in the case of a linear strip by virtue of the geometry of the curved strip. Moreover, the scanning angle is considerably larger and thus increases from 90° to 150°, for example.

However, it is possible that, for the formation of an image, the number of transducers employed for the center is greater than the number employed for the edges, thus resulting in higher resolution of the image at the center than at the edge. This is not very objectionable since, in medical imagery, the image is centered on the point of interest whilst the edges serve mainly to locate the element of interest with respect to the other organs. Thus a very wide field of view provides the physician in charge of diagnostic procedures with high convenience of examination and very high resolution at the center is conducive to fine diagnosis.

The invention is mainly directed to an imaging device and to a method for utilizing said device as described in the appended claims.

BRIEF DESCRIPTION OF THE DRAWINGS

In FIGS. 1 to 3, the same references have been used to designate the same elements.

DESCRIPTION OF THE PREFERRED EMBODIMENTS

Figure 1:
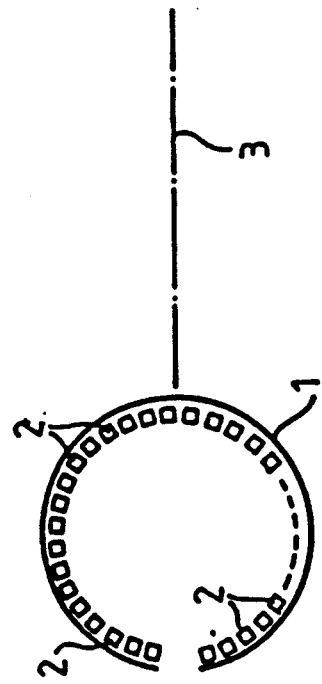
FIG. 1 is a diagram of a first example of construction of probes in accordance with the present invention.

In FIG. 1, there is shown an ultrasonic scanning probe 1 comprising a plurality of electroacoustic transducers 2 which are advantageously in uniformly spaced relation. In the example illustrated in FIG. 1, the probe has the shape of a circular arc. It is readily apparent that other shapes such as, for instance, a hyperbola, an elliptic arc or a parabola would not constitute any departure from the scope of the present invention.

The probe 1 has an axis of symmetry 3. At the time of formation of images, it will be an advantage to place the point of interest on the axis 3. The probe 1 is capable of forming images in a sector which is centered on the axis 3. Sector scanning will be obtained by applying variable time-delays to the transducers 2.

In the example illustrated in FIG. 1, the probe 1 is not provided with any transducers opposite to the axis 3. In point of fact, such transducers could never contribute to an image of a sector which is centered on the axis 3. The electroacoustic transducers are preferably piezoelectric transducers.

Figure 2:
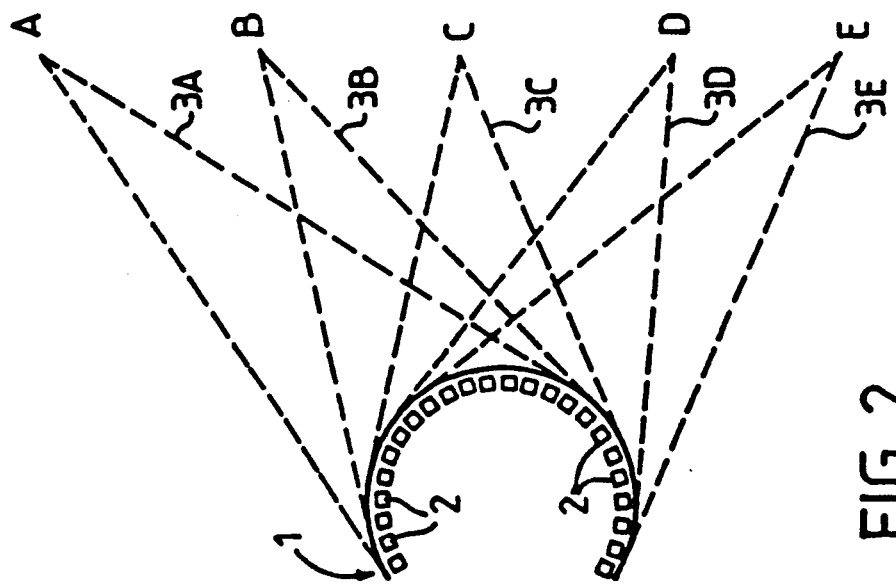
FIG. 2 is an explanatory diagram of the principle of operation of the probe in accordance with the present invention.

In FIG. 2, there is provided an explanatory diagram of image formation of a sector limited by the points A and E. The probe 1 is provided with a plurality of electroacoustic transducers 2 disposed at uniform intervals on a circle in the example of construction illustrated in FIG. 2. In the method proposed by the present invention, a point is insonated by focusing the ultrasound energy in an electronic scan. In other words, time-delays are applied to the signals generated by the transducers 2 so as to compensate for differences in operating speed. In the first place, however, the electroacoustic transducers 2 have intrinsic directivity and, in the second place, the geometry of the probe 1 does not enable all the electroacoustic transducers 2 to illuminate all the points of the object to be observed. In the device in accordance with the present invention, there are employed only those electroacoustic transducers 2 which are capable of insonating a point in order to obtain an image of that point. This principle is valid both in the case of a two-dimensional electronic scan in which each transmission will correspond to one line of the image and in the case of a three-dimensional electronic scan in which each transmission will correspond to one point of the image.

Thus in respect of each point A, B, C, D and E, there are employed all the electroacoustic transducers 2 whose orientation and directivity permit insonation of these points.

As shown in FIG. 2, the sectors 3a, 3b, 3c, 3d and 3e represent transducers which are capable of insonating the point or the lines which pass through the points A, B, C, D and E respectively.

Figure 3:
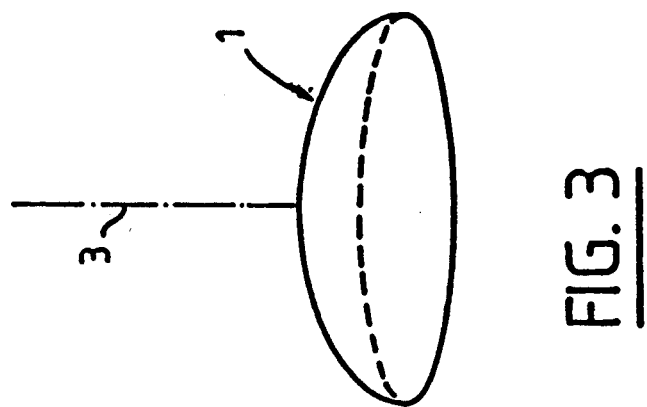
FIG. 3 is a diagram of a second example of construction of a probe in accordance with the present invention.

In FIG. 3, there is shown a spherical cap or segment which is capable of serving as a support for a probe 1. The distribution of the electroacoustic transducers 2 (not shown in FIG. 3) on a spherical segment permits three-dimensional focusing of the acoustic energy beam. The beams can be directed either by performing a three-dimensional electronic scan or by grouping the transducers together in rings and by associating with these rings addressing means corresponding to the various regions of the space to be scanned. The method just mentioned has been described in Pat. No. 83 016550 filed on Oct. 18th, 1983 by the CGR Ultrasonic Company.

Figure 5:
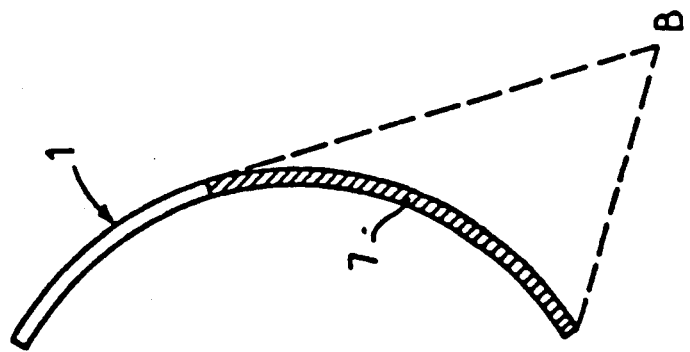
FIG. 5 is an explanatory diagram of operation of the probes in accordance with the present invention.
Figure 4:
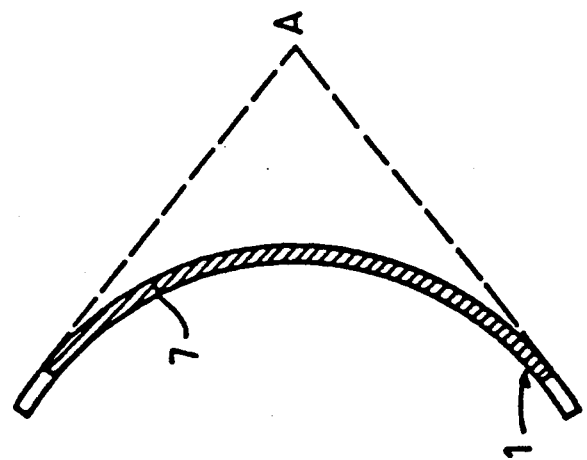
FIG. 4 is an explanatory diagram of operation of probes in accordance with the present invention.

FIGS. 4 and 5 show the influence of the incidence on which one line of the image is formed on the resolution of this part of the image.

FIG. 4 shows the principle of formation of the image of a line which passes through a point A located near the axis of the probe 1. All the electroacoustic transducers which form part of the shaded zone 7 take part in the formation of the image line which passes through the point A (not shown in FIG. 4). All the electroacoustic transducers which form part of the zone 7 are capable of insonating the point A. The line which passes through the point A will constitute on the display screen a line of the center of the image. The formation of this line has taken part in a zone 7 having a maximum number of electroacoustic transducers. There will thus be very high resolution at the center of the image at which the center of interest will be placed, namely the center of interest for the physician, for example.

In FIG. 5, there is shown the principle of formation of the image of a line which passes through a point B remote from the axis of the probe 1. In this case, the zone 7 of the electroacoustic transducers (not illustrated in the figure) which are capable of insonating the point B is smaller than in the case of FIG. 4. As the distance to the edge of the image decreases, so the zone 7 is reduced together with the resolution of the image. There is obtained on the edge of the image a reduced resolution corresponding to the resolution of systems of the prior art.

On the other hand, the use of electronic scanning associated with a curved strip makes it possible to obtain a larger scanning angle which increases for example from 90° in devices of known types to 150°.

Thus in the field of medical imaging, an image is obtained which has very high resolution at the center and offers a large scanning angle. In medical imaging, the edges serve mainly to locate the organs with respect to each other and therefore to identify them without requiring very high resolution. On the other hand, the organ which is to be examined and which calls for maximum resolution is placed at the center of the image. Frequently the physician who uses the device in accordance with the present invention will not even notice the reduction in resolution at the edge.

It is clearly possible to extend the probe 1 for example in order to form almost a full circle as illustrated in FIG. 1, without departing from the scope of the present invention. In this case, the resolution will be the same at the center and at the edge of the image at the cost of an increase in the number of transducers which are necessary for the utilization of a probe. Moreover, this makes it possible to increase the scanning angle.

On the other hand, in the case of a given number of transducer elements such as 128 or 256, for example, a limited curvature makes it possible to increase the resolution at the center.

Figure 6:
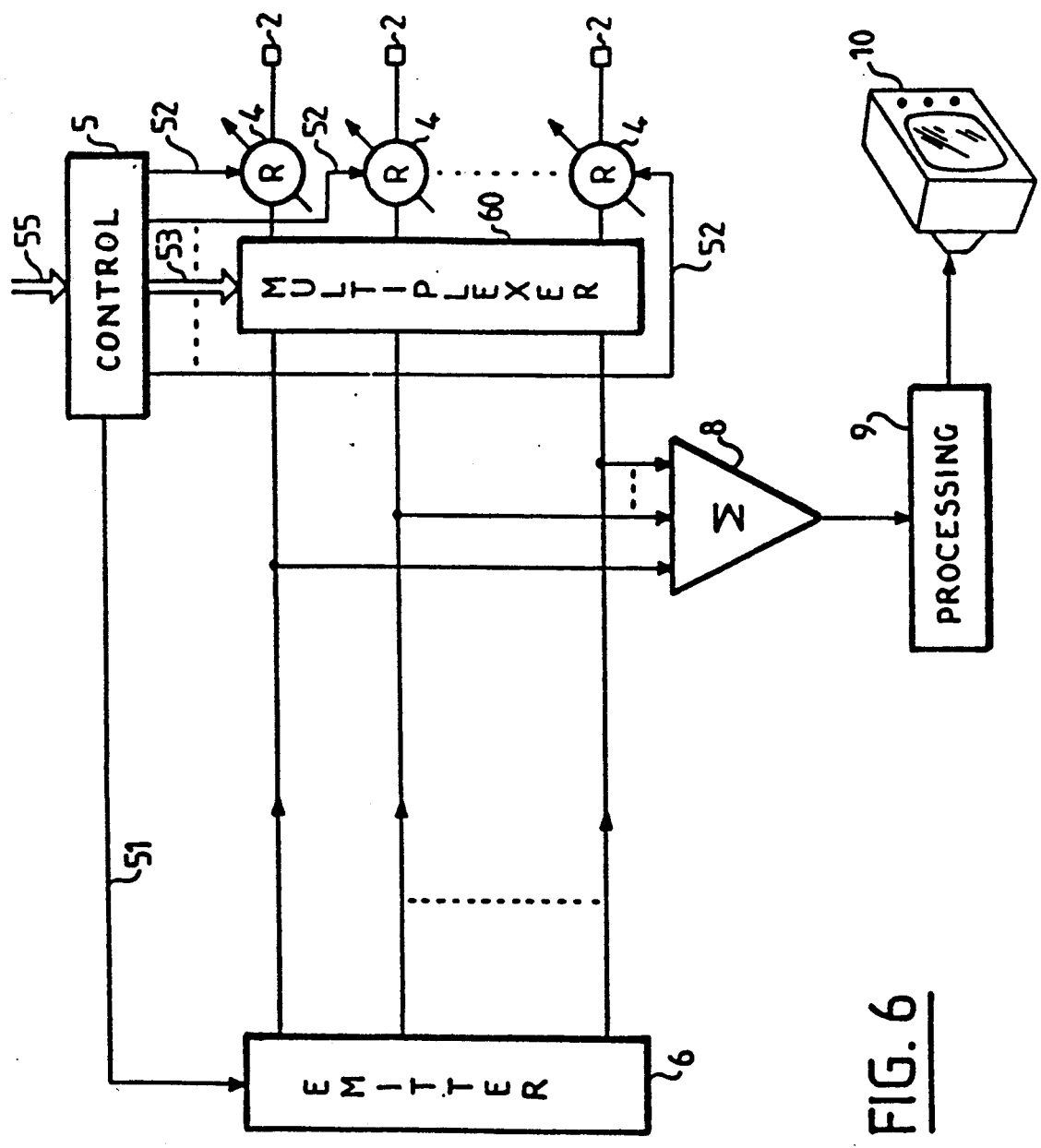
FIG. 6 is a diagram of a first example of construction of the imaging device in accordance with the present invention.

In FIG. 6, there can be seen a first example of construction of an ultrasonic scanning device in accordance with the present invention. The device comprises a plurality of electroacoustic transducers 2. In order to simplify the figure, the electroacoustic transducers 2 are represented as being in aligned relation. It is clearly apparent that any desired geometry such as, for example, a convex radiating surface can be adopted for the realization of the device in accordance with the present invention. The electroacoustic transducers 2 receive electrical energy through a multiplexing device 60 and a variable-delay device 4. The electroacoustic transducers 2 are connected through delay devices 4 and multiplexers 60 to a receiver 8. Said receiver 8 is connected to a signal-processing device 9. The signal-processing device 9 is connected to a utilization device 10 such as, for example a display device comprising, for example, a cathode-ray tube, an image memory, an image storage device or an image processing device. A control device 5 is connected to the delay device 4 by means of leads 52, to the multiplexer 60 by means of a bus 53 and to the transmitter 6 by means of a control line 51.

The control device 5 determines the electro-acoustic transducer 2 to be put into operation for each line of the image, controls the setting of the multiplexer 60 so as to permit this operation and controls the setting of a delay device 4 in order to obtain the desired focusing. Only those transducers which are intended to take part in a transmission are supplied by the transmitter 6 via the multiplexer 60.

At the time of reception, at least those transducers 2 which have taken part in the transmission are connected to the receiver 8 via the multiplexer 60.

By means of the line 51, the control device 5 ensures synchronization between transmission and reception. It is in fact important to ensure that the transmitter 6 does not transmit during reception in order to prevent the signal of the transmitter 6 from disturbing the operation of the receiver 8. Indeed, if no precautions are taken, the signal of the transmitter 6 is liable to saturate the receiver 8.

By way of example, the multiplexer 60 comprises a cascade-connected assembly of analog multiplexers such as, for instance, the analog multiplexer marketed under the reference DG 507 by the Siliconix Company.

It will be readily apparent that the use of a digital multiplexer does not depart from the scope of the present invention.

The delay elements 4 are for example delay lines, the time-delay being selected by switching a signal data path in the delay lines.

By way of example, the signal-processing device 9 comprises signal processors, filters, multipliers, adders and/or high-speed Fourier-transform computers.

The control device 5 ensures good operation of the device in accordance with the present invention. The device performs addressing, synchronization of transmissions and receptions. Various types of control device 5 may be employed. A suitable type of control device which can be mentioned by way of example has a sequencer provided with counters for addressing a memory in which the addresses to be employed are stored. Advantageously, the control device 5 includes at least one arithmetic and logic unit which may, for instance, be contained in a microprocessor, a read-only memory containing the program and an empty working memory.

Advantageously, the control unit 5 receives control orders from the user via a control bus 55.

Figure 7:
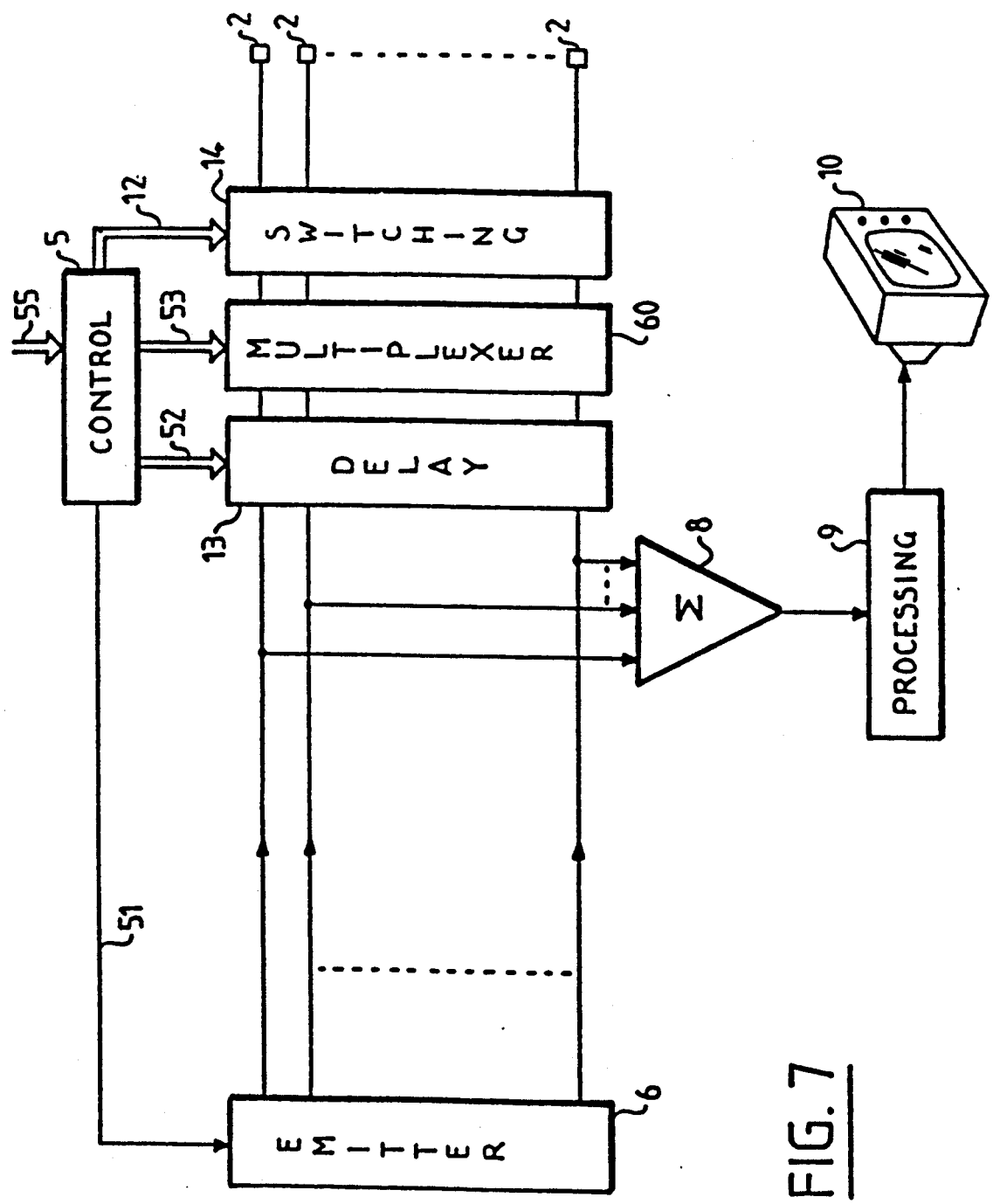
FIG. 7 is a diagram of a second example of construction of an imaging device in accordance with the present invention.

In FIG. 7, there can be seen a second example of construction of the device in accordance with the present invention. In this embodiment, the transmitter 6 and the receiver 8 are connected to the electroacoustic transducer 2 via a delay device 13, a multiplexer 60 and a switching device 14 connected in series. The control unit 5 is connected to the delay device 13 via a bus 52, to the multiplexer 60 via a bus 53 and to the switching device 14 via a bus 12. In addition, the control unit 5 is connected to the transmitter 6.

The delay device 13 is provided with delay lines which are capable of being connected in series and/or in parallel. Thus t):e delay device 13 makes it possible to obtain simultaneously the various values of time-delay which are necessary for operation of the probe. The switching device 14 associated with the multiplexer 60 serves to connect the requisite delay elements to the requisite electroacoustic transducer 2. The device as illustrated in FIG. 7 has the advantage of reducing the numbers of delay lines required for good operation of the device.

Figure 8:
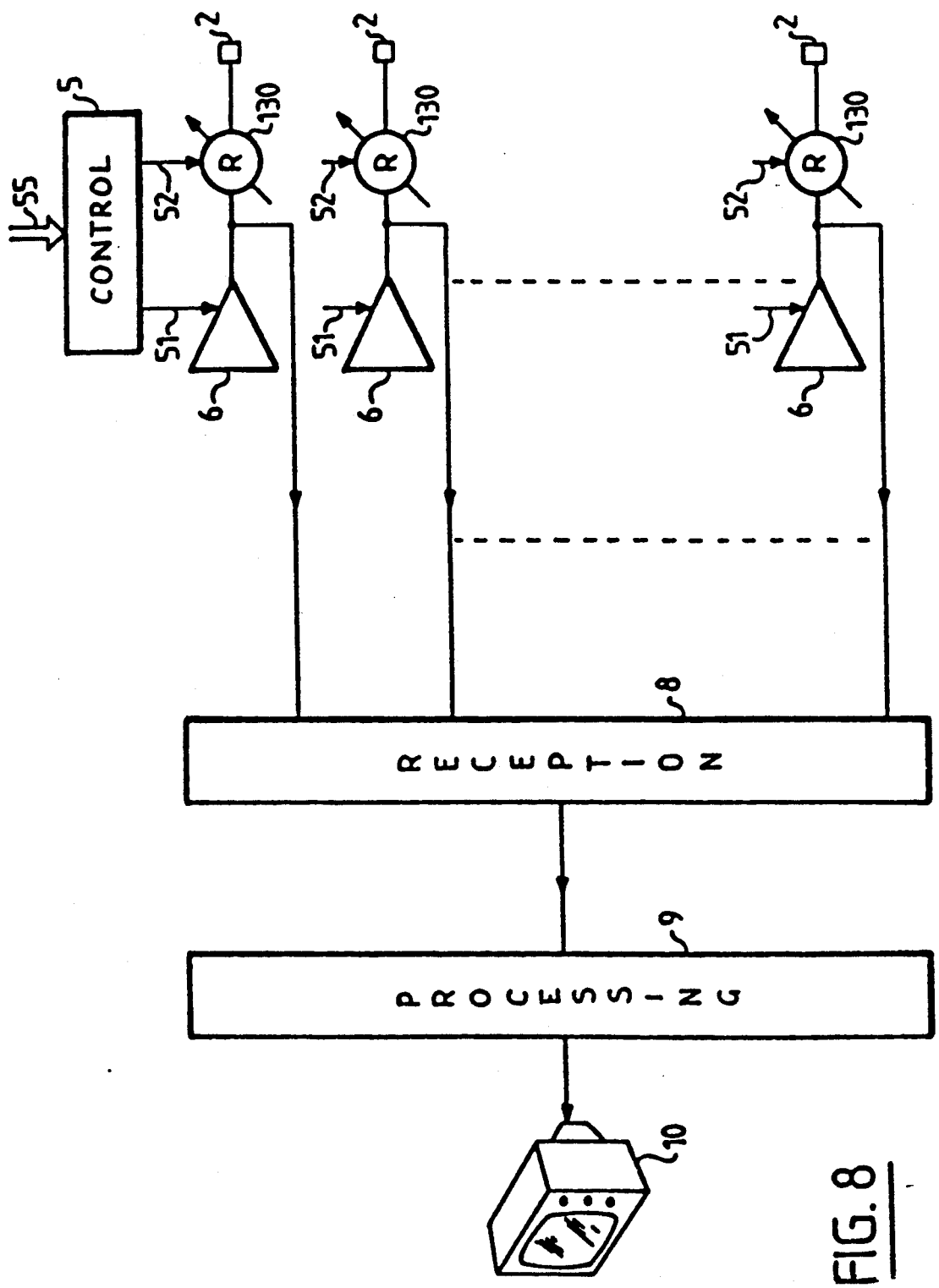
FIG. 8 is a diagram of a third example of construction of an imaging device in accordance with the present invention.

In FIG. 8, there is shown a third example of construction of the device in accordance with the present invention. In the example illustrated in FIG. 8, a transmitter 6 and a delay element 130 is associated with each electroacoustic transducer 2. The control device 5 is connected to the transmitters 6 via control lines 51 and to the delay elements 130 via control lines 52.

The electroacoustic transducers 2 are connected to a receiver 8 via delay elements 130. The receiver 8 is connected to a signal-processing device 9. Said signal-processing device 9 is connected to a utilization device 10 such as a display device, for example.

The invention applies to imagery involving the use of acoustic waves such as ultrasonic waves, for example. The invention is applicable in particular to nondestructive testing, to the production of images within liquids such as, for example, underwater images.

Finally, the invention finds one of its chief applications in the field of ultrasonic medical imaging.

What is claimed is:

1. An ultrasonic scanning device comprising:
   a plurality of piezoelectric transducers located on a convex surface;
   a plurality of delay elements capable of inducing a delay in the signals associated with said piezoelectric transducers, and
   switching means for activating a number of transducers as a function of a direction of shooting such that a smaller number of transducers are activated when said shooting direction is near the edge of a field than when said shooting direction is toward a center of said field so as to permit an optimum acoustic excitation of said direction, there being a common core of utilized transducers from any one direction to any adjacent direction.

2. An ultrasonic scanning device according to claim 1, wherein the piezoelectric transducers are located on a convex circle axis.

3. A device according to claim 1, wherein the piezoelectric transducers are located on a segment of a sphere.

4. A device according to claim 3, wherein said device comprises an automatic control device for determining the piezoelectric transducers to be utilized in order to transmit and/or receive an acoustic wave in respect of each azimuth, for determining the values of time-delays to be applied to the active transducers and for carrying out transmission/reception synchronization.

* * * * *

UNITED STATES PATENT AND TRADEMARK OFFICE
CERTIFICATE OF CORRECTION

PATENT NO. : 5,027,659

DATED : Jul. 2, 1991

INVENTOR(S) : Robert Bele, Patrick Bertrand, Jean-Pierre Ramond

It is certified that error appears in the above-identified patent and that said Letters Patent is hereby corrected as shown below:

Title page, item [73]:
The Assignee of the Invention, instead of "General Electric CBR SA, Les Moulinequx, France," should read:

GENERAL ELECTRIC CGR SA, ISSY les MOULINEAUX, France.

Signed and Sealed this

Twenty-third Day of March, 1993

*Attest:*

STEPHEN G. KUNIN

*Attesting Officer*     *Acting Commissioner of Patents and Trademarks*